United States Patent
Seth et al.

(10) Patent No.: US 9,567,651 B2
(45) Date of Patent: Feb. 14, 2017

(54) SYSTEM AND METHOD FOR THE DETECTION OF ABNORMALITIES IN A BIOLOGICAL SAMPLE

(75) Inventors: Subhendu Seth, Bangalore (IN); Sarif Kumar Naik, Bangalore (IN); Shankar Mosur Venkatesan, Bangalore (IN); Sunil Kumar, Bangalore (IN); Keswarpu Payal, Bangalore (IN); Sanjay Jayavanth, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 13 days.

(21) Appl. No.: 14/343,427

(22) PCT Filed: Sep. 11, 2012

(86) PCT No.: PCT/IB2012/054708
§ 371 (c)(1),
(2), (4) Date: Mar. 7, 2014

(87) PCT Pub. No.: WO2013/038331
PCT Pub. Date: Mar. 21, 2013

(65) Prior Publication Data
US 2014/0227682 A1 Aug. 14, 2014

Related U.S. Application Data

(60) Provisional application No. 61/534,031, filed on Sep. 13, 2011.

(51) Int. Cl.
*C12Q 1/70* (2006.01)
*G06T 7/00* (2006.01)
*G06K 9/00* (2006.01)

(52) U.S. Cl.
CPC ............... *C12Q 1/70* (2013.01); *G06K 9/0014* (2013.01); *G06K 9/00147* (2013.01);
(Continued)

(58) Field of Classification Search
CPC .... C12Q 1/70; G06K 9/0014; G06K 9/00147; G06T 7/0012; G06T 7/0014; G06T 2207/30024
(Continued)

(56) References Cited

U.S. PATENT DOCUMENTS 5,257,182 A 10/1993 Luck et al.
5,828,776 A 10/1998 Lee et al.
(Continued)

OTHER PUBLICATIONS

Plissiti et al. Combining Shape, Texture and Intensity Features for Cell Nuclei Extraction in PAP Smear Images. Pattern Recognition Letters 32 (6): 838-853 (Apr. 2011)—Full Text: pp. 1-28 version.*
(Continued)

*Primary Examiner* — Gail R Gabel

(57) ABSTRACT

A method or system detects abnormalities in a biological sample cells. The method or system performs at least the following steps, or is capable to carry out at least the following steps, respectively: a) acquiring an image of the sample by digital image acquisition, b) optionally, carrying out digital image processing, c) selecting a field of view, d) determining, by digital image processing, whether or not, in the field of view, cell aggregates exist, and e1) selecting a new field of view and carrying on with step c) if, in step d), it turns out that, in the field of view, the determination of cell aggregates is negative, or e2) carrying out further process steps if in step d), it turns out that, in the field of view, the determination of cell aggregates is affirmative.

17 Claims, 13 Drawing Sheets

(52) U.S. Cl.
CPC .......... *G06T 7/0012* (2013.01); *G06T 7/0014* (2013.01); *G06T 2207/30024* (2013.01)

(58) Field of Classification Search
IPC ........ C12Q 1/70; G06K 9/0014; G06T 7/0012
See application file for complete search history.

(56) References Cited

U.S. PATENT DOCUMENTS

| | | | |
|---|---|---|---|
| 5,978,498 A | 11/1999 | Wilhelm et al. | |
| 5,987,158 A | 11/1999 | Meyer et al. | |
| 6,026,174 A | 2/2000 | Palcic et al. | |
| 6,327,377 B1 | 12/2001 | Rutenberg et al. | |
| 6,379,907 B1* | 4/2002 | Liao .................. | C07K 16/3069 435/4 |
| 6,681,035 B1 | 1/2004 | Bamford et al. | |

OTHER PUBLICATIONS

Zhang et al. Cervical Cancer Detection Using SVM Based Feature Screening. MICCAI 2004. LNCS 3217: 873-880 (2004).*
Harandi et al. An Automated Method for Segmentation of Epithelial Cervical Cells in Images of ThinPrep. Journal of Medical Systems 34 (6): 1043-1058 (Dec. 2010) (Abstract Only).*
Boykov, Y., et al.; An Experimental Comparison of Min-Cut/Max-Flow Algorithms for Energy Minimization in Vision; 2004; IEEE Trans. on Pattern Analysis and Machine Intelligence; 26(9)1124-1137.
Bozzo, J., et al.; Red blood cells aggregability is increased by aspirin and flow stress, whereas dipyridamole induces cell shape alterations: measurements by digital image analysis; 1996; European Journal of Clinical Investigation; 26:747-754.
Chang, A. R., et al.; Can Technology Expedite the Cervical Cancer Screening Process? A Hong Kong Experience Using the AutoPap Primary Screening System with Location-Guided Screening Capability; 2002; American Journal of Clinical Pathology; 117(3).
Cheng, J., et al.; Segmentation of Clustered Nuclei with Shape Markers and Marking Function; 2009; IEEE Trans. on Biomedical Engineering; 56(3)741-748.
Clocksin, W. F.; Automatic segmentation of overlapping nuclei with high background variation using robust estimation and flexible contour models; 2003; Image Analysis and Processing; abstract.
Feng, X.; Image Segmentation Using Global Optimal Contour; 2003; 9 pages. http://www.cse.sc.edu/-Songwang/CourseProj/2003/Feng-report.pdf.
Fowler, J. D., et al.; Hydraulic Permeability of Immobilized Bacterial Cell Aggregates; 1991; Applied and Environmental Microbiology; 57(1)102-113.
Harandi, N. M., et al.; An Automated Method for Segmentation of Epithelial Cervical Cells in Images of ThinPrep; 2010; Journal of Medical Systems; 34(6)1043-1058.
Hislop, T. G., et al.; Cervical Cancer Screening in Canadian Native Women: adequacy of the Papanicolaou smear; 1994; Acta Cytologica; 38(1)29-32.
Kale, A., et al.; Segmentation of Cervical Cell Images; 2010; Int'l Conf. on Pattern Recognition; pp. 2399-2402.
Lassouaoui, N., et al.; Genetic algorithms and multifractal segmentation of cervical cell images; 2003; Proc. of 7th Intl. Symposium on Signal Processing and its Applications; vol. 2:1-4.
Li, Z. et al.; Biomedical Image Segmentation Based on Shape Stability; 2007; IEEE Trans. on Int. Conf. on Image Processing; pp. 281-284.
Liao, P., et al.; A Fast Algorithm for Multilevel Thresholding; 2001; J. of Information Science and Engineering; 17:713-727.
Mat-Isa, N. A., et al.; An automated cervical pre-cancerous diagnostic system; 2008; Artificial Intelligence in Medicine; 42(1)abstract.
Munn, L. L., et al.; Analysis of lymphocyte aggregation using digital image analysis; 1993; Journal of Immunological Methods; 166:11-25.
Phansalkar, N., et al.; Adaptive Local Thresholding for Detection of Nuclei in Diversely Stained Cytology Images; 2011; ICCSP; pp. 218-220.
Plissiti, M. E., et al.; Automated segmentation of cell nuclei in PAP smear images; 1994; IEEE Intl. Special topic Conference on Information Technology in Biomedicine; pp. 1-4.
Plissiti; M. E., et al.; Combining Shape, Texture and Intensity Features for Cell Nuclei Extraction in Pap smear images; 2011; Pattern Recognition Letters; 32(6)838-853.
Plissiti, M. E., et al.; Watershed-based segmentation of cell nuclei boundaries in Pap smear images; 1994; IEEE Intl. Special topic Conference on Information Technology in Biomedicine; pp. 1-4.
Shapiro, A., et al.; Raman Molecular Imaging: A Novel Spectroscopic Technique for Diagnosis of Bladder Cancer in Urine Specimens; 2011; European Urology; pp. 106-112.
Walker, R. F., et al.; Classification of Cervical Cell Nuclei Using Morphological Segmentation and Textural Feature Extraction; 1994; IEEE Proc. of 2nd Australian and New Zealand Conf. on Intelligent Information Systems; pp. 297-301.
Zhang, J., et al.; Cervical Cancer Detection Using SVM Based Feature Screening; 2004; LNCS; 3217:873-880.

* cited by examiner

A

B

A

B

A            B

SYSTEM AND METHOD FOR THE DETECTION OF ABNORMALITIES IN A BIOLOGICAL SAMPLE

CROSS REFERENCE TO RELATED APPLICATIONS

This application is a national filing of PCT application Serial No. PCT/IB2012/054708, filed Sep. 11, 2012, published as WO 2013/038331 A1 on Mar. 21, 2013, which claims the benefit of U.S. provisional application Ser. No. 61/534,031 filed Sep. 13, 2011, which is incorporated herein by reference.

FIELD OF THE INVENTION

The invention relates to the field microscopic detection of abnormalities in a biological sample comprising cells.

BACKGROUND OF THE INVENTION

Cancer arising from cervix is the number one cancer in women in many industrialized countries as well as emerging countries. About 30% of cancers in women are due to cervical cancer with more than 100,000 new cases diagnosed every year, e.g., in India. The estimated compounded annual growth rate (CAGR) for cervical cancer cases is 2.56% and at this growth rate approximately 175,000 new cases of cervical cancer will be detected in the year 2012.

One of the recommended tools for screening of cervical cancer is to detect cytological precursors of cancer in Papanicolaou tests (also called Pap-smear, Pap-test, cervical smear, or smear test), which is a screening test used in gynecology to detect premalignant and malignant processes in the cervical canal especially in the transformation zone. In taking a Pap smear, a speculum is used to gather cells from the outer opening of the cervix of the uterus and the endocervix. The cells are examined under a microscope to look for abnormalities. The test aims to detect potentially pre-cancerous changes, which are, among others, caused by sexually transmitted human papilloma viruses. The test remains an effective, widely used method for early detection of pre-cancer and cervical cancer. The test may also detect infections and abnormalities in the endocervix and endometrium.

This procedure has been effective in bringing down the incidence of cervical cancer in the developed countries. However, Pap smear has a false negative rate of 10-29%. Reasons for the false-negative results are numerous and include sample collection errors (failure to obtain adequate cells on the slide in terms of cells representing the transformation zone), screening errors (failure to find abnormal cells on the slide), interpretation errors (failure to properly interpret abnormal cells), and miscellaneous laboratory errors related to staining problems, mislabeling, etc.

One of the major factors is that it is challenging for a pathologist to go through each of the cell in the slide. Each Pap smear slide has more than 10,000 cells of different morphological features. Depending on the stage of the cancer it is not unlikely that only a small fraction of cells (e.g., <<1%) in the sample is abnormal. This abnormality is detected by changes in the morphological features of the cell such as nuclear features, nuclear membrane, nuclear cytoplasmic ratio etc. Thus, careful observation of each cell feature is required to prevent false negative impression. This is a challenging task, considering the limited number of qualified pathologist in the field, the tremendous economical pressure under which they work, the limited time budget they have for each patient and the huge workload they are exposed to.

SUMMARY OF THE INVENTION

According to a first aspect of the invention, a method for the detection of abnormalities in a biological sample comprising cells is provided. Said method or system comprises at least the following steps, or is capable to carry out, and/or comprises means capable to carry out, at least the following steps, respectively:

a) acquiring an image of said sample by digital image acquisition
b) optionally, carrying out digital image processing
c) selecting a field of view
d) determining, by digital image processing, whether or not, in said field of view, cell aggregates exist, and
e1) selecting a new field of view and carrying on with step c) if, in step d), it turns out that, in said field of view, the determination of cell aggregates is negative, or
e2) carrying out further process steps if, in step d), it turns out that, in said field of view, the determination of cell aggregates is affirmative.

The term "cell aggregates", as used herein, refers to a group of at least two cells being in physical contact with one another and forming a two- or three-dimensional cluster.

The term "the determination of cell aggregates is negative" as used herein, means that no cell aggregates could be found in the actual field of view. The term "the determination of cell aggregates is affirmative" as used herein, means that cell aggregates have been found in the actual field of view, suggesting that the actual field of view could comprise abnormal cells.

The process according to the invention automatically scans the sample for fields of view which are likely to comprise images of abnormal cells which is usually the case for cells which appear in clusters, or aggregates. The approach thus carries out a preselection in which only those fields of view are passed over to further analysis which comprise images of cell aggregates, while those fields of view which do not comprise images of cell aggregates are discarded, because it is unlikely that they comprise images of abnormal cells. This again saves time and reduces computational efforts.

Further, this methodological approach comprises a feedback loop, which significantly reduces the computational time for complex image processing algorithms as well as it simplifies the tedious task of examining each of the cells found in the sample, namely by reducing the evaluation time. The approach does not analyse the acquired image as a whole, but selects subunits of said image, which are called "field of view" herein, for image processing. An overview of the described method is given in FIG. 1.

Generally, the cells which have the highest risk to become cancerous are ectocervical cells, while endocervical cells have a smaller risk to become cancerous (in which case an adenocarcinoma is formed). Ectocervical cells are also called squamous cells, while endocervical cells are also called columnar cells.

However, it has been observed that also cells which have only a small risk to become cancerous also tend to form aggregates, which may create some confusion under particular circumstances. In a preferred embodiment, the method according to the invention thus further comprises the steps of:

f) determining the degree of variation of at least one given morphological feature of at least two cells in the field of view, and g1) classifying the sample as "likely to comprise abnormal cells" if the degree of variation of said morphological feature exceeds a predetermined threshold, or g2) classifying the sample as "likely to comprise normal cells" if the degree of variation of said morphological feature falls below a predetermined threshold.

The term "classifying the sample as likely to comprise abnormal cells" is equivalent to "suspecting a sample for abnormality", as shown in FIG. 2. The term "classifying the sample as likely to comprise normal cells" is equivalent to "suspecting a sample for normal endocervical cells", as shown in FIG. 8, or, although clinically imprecise, "suspecting a sample for endocervical cells", as shown in FIG. 2.

As used herein, the term "abnormal cells" relates to cells which are in a process of becoming cancerous, or malignant, or are cancerous, or malignant, already.

Preferably, it is provided that said morphological feature is at least one selected from the group consisting of
cell nucleus size, or area
regularity of shape of a cell, and/or a cell nucleus
size ratio of cytoplasm to nucleus, in a given cell, and/or
ratio of areas of cytoplasm and nucleus, in a given cell.

In this complimentary approach, the variability of said morphological feature can be used as a further distinguishing feature, because in abnormal cell aggregates the nucleus size varies widely, whereas in normal cell aggregates the nucleus sizes remain uniform.

This complimentary approach thus serves to identify abnormal cells, particularly in those regions of interest which have earlier been identified, by cell aggregation analysis, as suspicious. If the variation said morphological feature in the field of view exceeds, statistically, a given threshold, the sample can be classified as "likely to comprise abnormal cells".

The cell nuclei sizes in the field of view can for example be determined by calculating the respective image area, e.g., by counting the number of pixels in the respective region. The variation of nuclei sizes in the field of view can for example be expressed as standard deviation of these areas, or by determining the variation in major axis or minor axis of the ellipse encircling these regions, or ratio of these values. While no fixed threshold value exists for the variation of sizes of the nuclei, thresholds can be determined a priori using ground truth data which could also vary on account other factors such as magnification, resolution of the image, etc.

The term "shape", as used herein, relates to the two-dimensional shape of a cell nucleus image, in the field of view. A cell nucleus shape is considered to have a high degree of regularity in case the shape of its image is circular, or close to circular. The criterion to determine the cellular shape is by employing properties like form factor, perimeter, major axis, minor axis cell membrane signature.

If the regularity of the cell nucleus shapes is, statistically, below a given threshold, the sample can as well be classified as likely to comprise abnormal cells.

The ratio of cytoplasm size, or area and nucleus size, or area, in a given cell, is another indicator which can be used in the context of the present invention. While normal cells have large cytoplasm and small nucleus, abnormal cells tend to have large nuclei and small cytoplasm.

The cellular Nucleus harbours the most significant changes in precancerous and cancerous cells. Hence, identifying the nucleus automatically can be a useful approach to detect abnormal cells in cervical smears. However, the segmentation of nucleus is a challenging task due to the varied morphological appearance with clumps and artifacts (see FIG. 15). Moreover, in some cases, the Pap smear images are blurry and highly affected by unwanted noises, e.g., blood, air artifacts (bubbles), or vagina discharge. In some cases, Pap-smear images of that kind may lead to an increase in false alarms when analyzed with a segmentation algorithm. Existing techniques are unable to tackle all these problems. Hence a fast and accurate nucleus segmentation technique is necessary to solve this issue.

According to a particularly preferred embodiment, the cell nucleus is therefore detected by an optical technique encompassing multilevel thresholding. Image histograms are usually the basis for thresholding. A histogram is unimodal if there is one hump, bimodal if there are two humps and multimodal if there are many humps. Histograms of Pap-smear images are multimodal in nature (see, e.g., FIG. 11A). According to this embodiment, multilevel thresholding has been introduced to locate initial seeds for nucleus segmentation. This is the first and foremost common step for all the above four methods.

In a more preferred embodiment, said optical technique encompassing multilevel thresholding is at least one selected from the group consisting of
IGMT (Information Gain-based Multilevel Thresholding technique)
IEMT (Information gain and color Edge-based Multilevel Thresholding technique)
IRMT (Information gain-based Recursive Multilevel Thresholding technique), and/or
IGTMT (Information and Graph Theory-based Multilevel Thresholding technique)

In IGMT, an information gain-based local region refinement is introduced after multiple thresholding to segment out nucleolus region. In IEMT, color edge analysis is introduced along with information gain to improve the accuracy of segmentation. However, region growing based on global multiple threshold levels may lead to chance of under/over segmentation of nuclei.

IRMT may be used to refine the region based on local multilevel thresholding, although it may be unable to solve the boundary leak problem. Hence, local boundary adjustment is necessary to solve this problem. IGTMT may be used to fine-tune the boundary region of Pap-smear nuclei. The different approaches will be discussed in detail in the following:

Information Gain-Based Multilevel Threshold (IGMT)

In this approach, information gain is employed along with clustering technique to segment out Pap-smear nuclei. Histograms of Pap-smear images are multimodal in nature. Hence in the first step (global processing) multilevel thresholding has been introduced to locate initial seed for nucleus segmentation. In the following step, information gain-based local region selection and refinement technique has been introduced to fine-tune and isolate the nucleus region (see FIG. 10 (A)). If change in multilevel threshold yields abrupt change in information gain for a particular region of interest (ROI), region growing using multilevel threshing stops.

Information Gain and Color Edge-Based Multilevel Thresholding (IEMT)

IGMT is capable of segmenting nucleus regions with higher accuracy than other threshold based techniques. However, due to unfocused Pap-smear images, improper staining and other artifacts discussed above, information gain may sometimes not be sufficient enough for region refinement. Hence, colour edge analysis is introduced along with information gain to fine-tune and isolate the nucleus region (see FIG. 10 (B)). If a change in multilevel threshold yields abrupt change in information gain as well as normalized color edge for a particular region of interest (ROI), region growing using multilevel threshing stops. This additional information (color edge) obtained with IEMT yields increasing accuracy of the nucleus segmentation than the IGMT method.

IGMT and IEMT methods are capable of finding the nucleus region in Pap-smear images. However, region growing for a ROI based on multiple threshold levels may lead to chance of under/over segmentation of nuclei (see, e.g., FIG. 11(B)).

Information Gain-Based Recursive Multilevel Thresholding (IRMT)

Recursive multilevel-based thresholding is introduced in IRMT to reduce the possibility of over/under segmentation of nuclei in IGMT and IEMT methods (see FIG. 7(A)). IRMT consists of two major steps: (i) global seed selection, followed by (ii) local region refinement.

Global seed selection of Pap-smear images as carried out in the IRMT method is identical to IGMT and IEMT. In case of a local region refinement, the IRMT method provides two major steps:

(ii.a.) Selection of upper and lower bound of threshold for individual region: First of all, optimal threshold t is computed using information gain and color edge for individual ROI. This optimal threshold t sometimes yields over/under segmented nuclei. Therefore, region ($R_{ub}$) having gray value in-between t−1 and t+1 and connected with the ROI ($R_t UR_{t+1}$) is chosen for farther processing (see FIG. 11(B)). The idea behind this step is that the exact nucleus boundary lies in between this bounding region ($R_{ub}$).

(ii.b.) Recursive multilevel threshold for region refinement: The same multilevel thresholding technique is applied on the histogram of bounding region ($R_{ub}$) (see FIGS. 12 (A) and (B)). Sub-thresholds thus obtained will increase the chance of getting more refined optimal threshold using information gain and color edge-based region growing method. This will help in fine-tuning the individual ROI obtained by the IGMT or IEMT method.

Information and Graph Theory-Based Multilevel Thresholding (IGTMT)

The proposed IRMT method may sometimes fails to solve the boundary leak problem. The basic idea behind the IGTMT approach is to utilize the graph cut theory for local boundary refinement (see FIG. 14 (B)).

Like the previous approaches, global multilevel thresholding is the first step in the IGTMT method, to carry out seed initialization of the probable region of the nucleus. This is followed by the selection of upper and lower bound of threshold for individual region which is similar to the IRMT method. Thereafter, to increase the accuracy of segmentation scheme, IGTMT introduces the min cut/max flow based graph theory approach. The IGTMT method uses the similarity measure based on gray level difference of neighbourhood pixels in $R_{ub}$ region. This affinity measures are used as weights in graph where image pixels are represents as nodes with pre-calculated single source and sink (see FIG. 13). Min cut finds a partitioning of graph nodes which minimizes the sum of weights of cut edges. This introduces the granularity concept helping to achieve the exact boundary of the nucleus.

In another preferred embodiment, it is provided that the method further comprises the step of determining at least one feature selected from the group of brightness intensity variation within a cell and/or a cell nucleus jazziness of a cellular membrane texture, and/or fractal dimension of the nucleus As used herein, the term "jazziness" shall mean the variation of distance between cell boundary points from centre of the cell or a fixed reference point preferably inside the cell. High jazziness in texture can be considered as an indication of abnormality.

As used herein, the term "texture" shall mean the spatial arrangements of colors or intensities in a nucleus or cell region. High variations in texture can be considered as an indication of abnormality.

As used herein, the term "fractal dimension of the nucleus" relates to a statistical quantity that gives an indication of how completely a fractal appears to fill space of a given cell, as one zooms down to finer and finer scales.

| morphological feature | algorithm/technique for determination |
|---|---|
| aggregation of cells | determining inter-nuclei distance |
| cell nucleus size, or area | calculating the respective image area, e.g., by counting the number of pixels in the respective region |
| inter-nuclei distance | distance between the centre of any two nucleus |
| regularity of shape of a cell, and/or a cell nucleus | employing properties like form factor, perimeter, major axis, minor axis cell membrane signature. |
| ratio of cytoplasm to nucleus in terms of size, or ratio of areas of cytoplam and nucleus size, or area, in a given cell | see cell nucleus size |
| Brightness/intensity variation within a cell and/or a cell nucleus | variance of intensity in the cell nucleus |
| jazziness of a cellular membrane | the variation of distance between cell boudry points from centre of the cell or a some fixed reference point prferably inside the cell |

| morphological feature | algorithm/technique for determination |
|---|---|
| Texture | the spatial arrangements of colors or intensities in a nucleus or cell region |
| fractal dimension of the nucleus to measure the deviation from the uniformity | Hausdorff dimension, box counting dimension, Renyi dimension |

In still another preferred embodiment, the method according to the invention further comprises at least one step selected from the group consisting of:
a) detailed inspection of the cervix by colposcopy;
b) carrying out a HPV DNA test in said biological sample, or in new sample with comparable properties;
c) carrying out a Biomarker test in said biological sample, or in new sample with comparable properties; and/or
d) visual inspection of said biological sample, or of a new sample with comparable properties, by a qualified pathologist.

Alternatively, the method according to the invention further comprises the step of recommending further investigation by at least one step selected from the group consisting of
a) detailed inspection of the cervix by colposcopy;
b) carrying out a HPV DNA test in said biological sample, or in new sample with comparable properties;
c) carrying out a Biomarker test in said biological sample, or in new sample with comparable properties; and/or
d) visual inspection of said biological sample, or of a new sample with comparable properties, by a qualified pathologist.

Colposcopy is a medical diagnostic procedure to examine an illuminated, magnified view of the cervix and the tissues of the vagina and vulva. Primarily in order to detect premalignant lesions and malignant lesions which may result in cancer. Colposcopy is done using a colposcope, which provides an enlarged view of the areas, allowing the colposcopist to visually distinguish normal from abnormal appearing tissue and take directed biopsies for further pathological examination. The main goal of colposcopy is to prevent cervical cancer by detecting precancerous lesions early and treating them.

A HPV DNA test detects cervical infection with human papilloma virus (HPV), which is one of the most important infectious causes of cervical cancer. 84% of new cervical cancers were in the developing world, compared with about 50% of all new cancers. HPV DNA test kits are today commercially available. Such test may be carried out during a routine smear test, as described above (in which case part of the smear sample is taken for the HPV DNA test, while another part is taken for the method according to the invention, or with a newly taken sample with comparable properties, and can be used to improve, confirm or falsify the diagnostic significance of the method according to the invention.

Biomarker tests have been developed to investigate whether or not a patient suspected to be predisposed for cervical cancer, or a patient who is suspected for having cervical cancer, or in which cervical cancer has already been diagnosed, has, in its genome or proteome, an abnormality which coincides with increased or decreased likelihood of getting a given cancer, or which coincides with increased or decreased responsiveness towards a given therapy. Such abnormality is, for example, a mutation in a given gene, an abnormality in an epigenomic feature, like DNA methylation, or an abnormality with respect to expression of a given gene.

In still another preferred embodiment of the method according to the invention, the image acquisition is carried out by means of a scanner. As an alternative, a two dimensional imaging device can be used. In both cases the imaging device is preferably a CCD (linear or two dimensional) or a CMOS (linear or two dimensional).

In another preferred embodiment of the method according to the invention, the image acquisition is carried out by means of an optical magnification device. Said optical magnification device is, for example, a microscope.

In still another preferred embodiment, the method according to the invention, further comprises, prior to step a), a step in which an image of the sample is acquired at lower magnification, as is the case in step a). In this embodiment, an overview image is made first. The low magnification slide overview is processed by the algorithm to identify the regions suspicious for abnormality and those suspected region are further scanned with higher magnification. This will provide an advantage of quick scanning of the slides. In yet another preferred embodiment of the method according to the invention, steps b) and following are carried out while the digital image acquisition and/or the digital image processing is still in process.

This methodological approach, which is also called "on the fly" or "real time", reduces the computational time for complex image processing algorithms as well as it simplifies the tedious task of examining each of the cells found in the sample by reducing the evaluation time.

Further, this approach allows to forgo an image archive of the raw images. In such embodiment, it is possible to only store only the selected processed images (see, e.g., FIG. 5), or even only the non-image data extracted from such images.

Further, such real time approach enables a pathologist/operator to intervene in the process, e.g., to fine tune discriminating variables, or to teach the system in that results of a given method step are accepted, or rejected as false.

In yet another preferred embodiment of the method according to the invention, step d) comprises at least the steps of
Segmentation of cell nuclei, and
Determining the centroids of each cell.

Preferably, the latter can be done by determining the inter-nuclei distance of at least two cells.

As used herein, the term "segmentation of cell nuclei" refers to the process of partitioning a digital image comprising the image of at least one cell into multiple segments (sets of pixels in order to identify the cell nuclei. More precisely, image segmentation is the process of assigning a label to every pixel in an image such that pixels with the same label share certain visual characteristics. The result of image segmentation is a set of segments that collectively cover the entire image, or a set of contours extracted from the image (see edge detection). Each of the pixels in a region are similar with respect to some characteristic or computed property, such as color, intensity, or texture. Adjacent regions are significantly different with respect to the same characteristic(s). When applied to a stack of images, typical in Medical imaging, the resulting contours after image segmentation can be used to create 3D reconstructions with the help of interpolation algorithms like marching cubes.

As used herein, the term "centroid of a cell" relates to the geometric center, or barycenter, of a cell's two-dimensional image, as determined with digital image processing methods, e.g., by image moments.

In another preferred embodiment of the present invention, the biological sample comprising cells is a cervical sample. However, because principles of cancer genesis and cell transformation are ubiquitous, the method can also be used with samples from other body tissues which have to be checked for abnormalities, like breast samples, prostate samples, liver samples, lung samples and so forth.

In case the biological sample comprising cells is a cervical sample, it is further preferred the method further comprises at least one step selected from the group consisting of:
  classifying cells comprised in a sample which is likely to comprise normal cells as "normal endocervical" or "normal ectocervical" based on a set of predetermined criteria, and/or
  classifying cells comprised in a sample which is likely to comprise abnormal cells as "abnormal endocervical or "abnormal ectocervical" based on a set of predetermined criteria.

It is again important to mention that the term "ectocervical cells" is used, interchangeably, with the term "squamous cells" herein.

Furthermore, it is preferred that the method according to the invention further comprises at least one step of counting a given cell type, or updating an existing count thereof.

It is further preferred that the biological sample comprising cells comprises at least one sample selected from the group consisting of
  smear sample
  tissue slice
  liquid sample, and/or
  any other cytology sample.

A smear sample is for example similar or identical to those samples used in the Papanicolaou tests (also called Pap smear, Pap test, cervical smear, or smear test). A tissue slice is for example, sliced by a microtome. A liquid sample can preferably consist of a suspension of cells, e.g., obtained by a smear.

Other suitable samples comprise, but are not restricted to, fine needle aspiration cytology (FNAC) samples, abrasive cytology samples and/or exfoliated samples.

It needs to be said that in the flow charts, the term slide is used. In many cases a sample is indeed placed on a slide to make it available for investigation, e.g. a tissue slice, or a smear. However, other devices can also be used to carry a sample, e.g. a small cuvette in case the sample is a liquid sample or a cartridge in case the sample is a brush sample. The term slice as used in the flow charts is thus by no means construed to limiting the scope of the present invention.

In a particularly preferred embodiment of the present invention, the biological sample comprising cells is stained, preferably prior to step a) of image acquisition. Dyes which are preferably used comprise Pap-stain, ultra fast Pap-statin, Romanowsky-type stain, Haris Haematoxylin stain, fluorescent stains like Achrodyn Orange, and H & E stain.

In another preferred embodiment of the method according to the invention optical and/or digital image enhancement approaches are used.

Optical image enhancement is preferably carried out prior to step a) of image acquisition. Preferred methods, though non-limiting, comprise dark field microscopy, phase contrast, differential interference contrast (DIC) and/or reflected interference contrast (RIC). Digital contrast enhancement is preferably carried out after step a) of image acquisition. Preferred methods comprise bright field microscopy, for example a typical transmission microscope.

In still another preferred embodiment of the method according to the invention steps b) and following are carried out while the data related to the acquired image, or parts thereof, is still in a volatile memory.

As used herein, the term volatile memory is used interchangeably with the term temporary memory, and shall be understood in such way that the data related to the acquired image are not yet stored on the hard disk or on a flash storage. A preferred form of such volatile memory is a random access memory (RAM) used by the image processor, or by the computer's CPU.

According to still another aspect of the invention a system for the detection of abnormalities in a biological sample comprising cells is provided. The system is capable to carry out, and/or comprises means capable to carry out, at least the following steps:
  a) acquiring an image of said sample by digital image acquisition
  b) optionally, carrying out digital image processing
  c) selecting a field of view
  d) determining, by digital image processing, whether or not, in said field of view, cell aggregates exist, and
  e1) selecting a new field of view and carrying on with step c) if, in step d), it turns out that, in said field of view, the determination of cell aggregates is negative, or
  e2) carrying out further process steps if, in step d), it turns out that, in said field of view, the determination of cell aggregates is affirmative.

It is particularly preferred that said system is further capable to carry out, and/or comprises further means capable to carry out said the steps of:
  f) determining the degree of variation of at least one given morphological feature of at least two cells in the field of view, and
  g1) classifying the sample as "likely to comprise abnormal cells" if the degree of variation of said morphological feature exceeds a predetermined threshold, or
  g2) classifying the sample as "likely to comprise normal cells" if the degree of variation of said morphological feature falls below a predetermined threshold.

Further, said system is preferably capable to carry out, and/or comprises further means capable to carry out the other method steps discussed above.

According to still another aspect of the invention a device for the detection of abnormalities in a biological sample comprising cells, is provided. The device comprises at least the following items:
  a sample receiving unit for receiving the biological sample
  a digital image acquisition unit for acquiring a digital image of the sample
  a digital image processing unit for carrying out at least one of the method steps according to the invention, and
  a user interface comprising at least one output means and one input means.

Said output means is preferably a display, or a touch screen, while said input means is preferably an array of keys, or buttons, or a touchscreen.

It is important to mention that the method according to the invention is not restricted to the use in such device. It can also be used "stand-alone" for the detection of locations/regions in a slide or set of images being suspected to contain images of abnormal cells.

In a preferred embodiment, the device according to the invention further comprises at least one optical magnification unit.

In another preferred embodiment, the device according to the invention further comprises at least one interface for connecting the device with other equipment. Such interface is, preferably, a GSM interface, a 3G interface, a USB interface, a Bluetooth interface, a Firewire interface and/or a WiFi interface, hypertext terminal, etc.

In another preferred embodiment, the device according to the invention further comprises at least one sample collector and/or at least one cartridge in which the sample is transferred, said cartridge being disposed for placement in the sample receiving unit.

The system are device discussed above is preferably in the form of a point of are device (POC). Preferably, it is provided as a handheld or desktop unit. Even more preferably, it is battery driven and/or portable.

According to another aspect of the invention, use of a method, a system and/or a device according to the invention for at least one purpose selected from the group of cancer screening cancer diagnosis prediction with respect to a given therapy, and/or concomitant monitoring of a given cancer therapy is provided.

BRIEF DESCRIPTION OF THE DRAWINGS

These and other aspects of the invention will be apparent from and elucidated with reference to the embodiments described hereinafter. In the drawings:

In FIG. 11 (B), $R_{t-1}$ is a single image region below $t-1^{th}$ threshold as seen in FIG. 11 (A), and $R_t$ is the region having gray value in-between $t-1^{th}$ and $t^{th}$ threshold as seen in FIG. 11 (A), and $R_{t+1}$ is region having gray value in-between $t^{th}$ and $t+1^{th}$ threshold as seen in FIG. 11 (A). The actual region boundary of the nucleus is marked by an arrow.

FIG. 12 (A) shows recursive multiple threshold levels $T_{r1}$ to $T_{rM}$ in ascending order between $t-1^{th}$ and $t+1^{th}$ threshold of FIG. 11 (A). FIG. 12 (B) shows regions thresholded by levels $T_{r1}$ to $T_{rM}$.

DETAILED DESCRIPTION OF EMBODIMENTS

Figure 1:
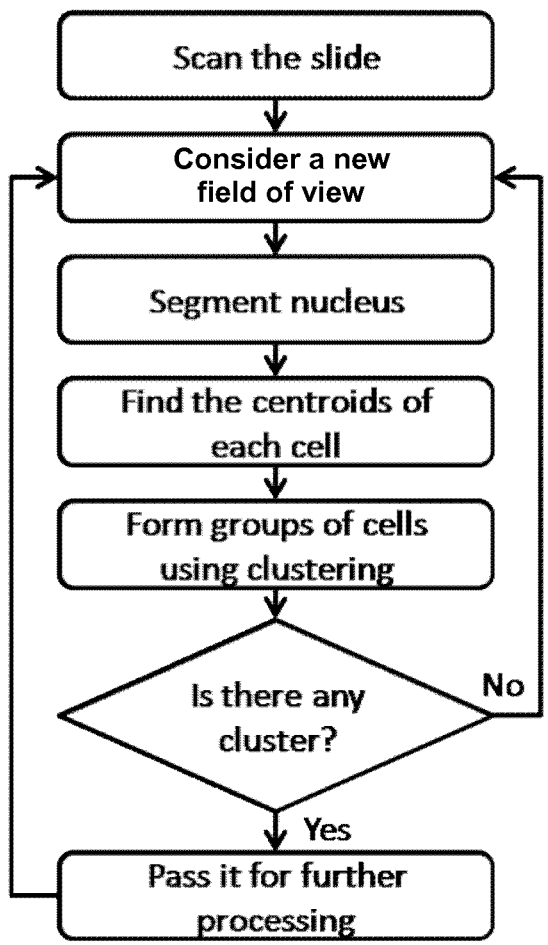
FIG. 1 shows a flow diagram identifying regions of interest for the presence or absence of cell aggregates.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Figure 2:
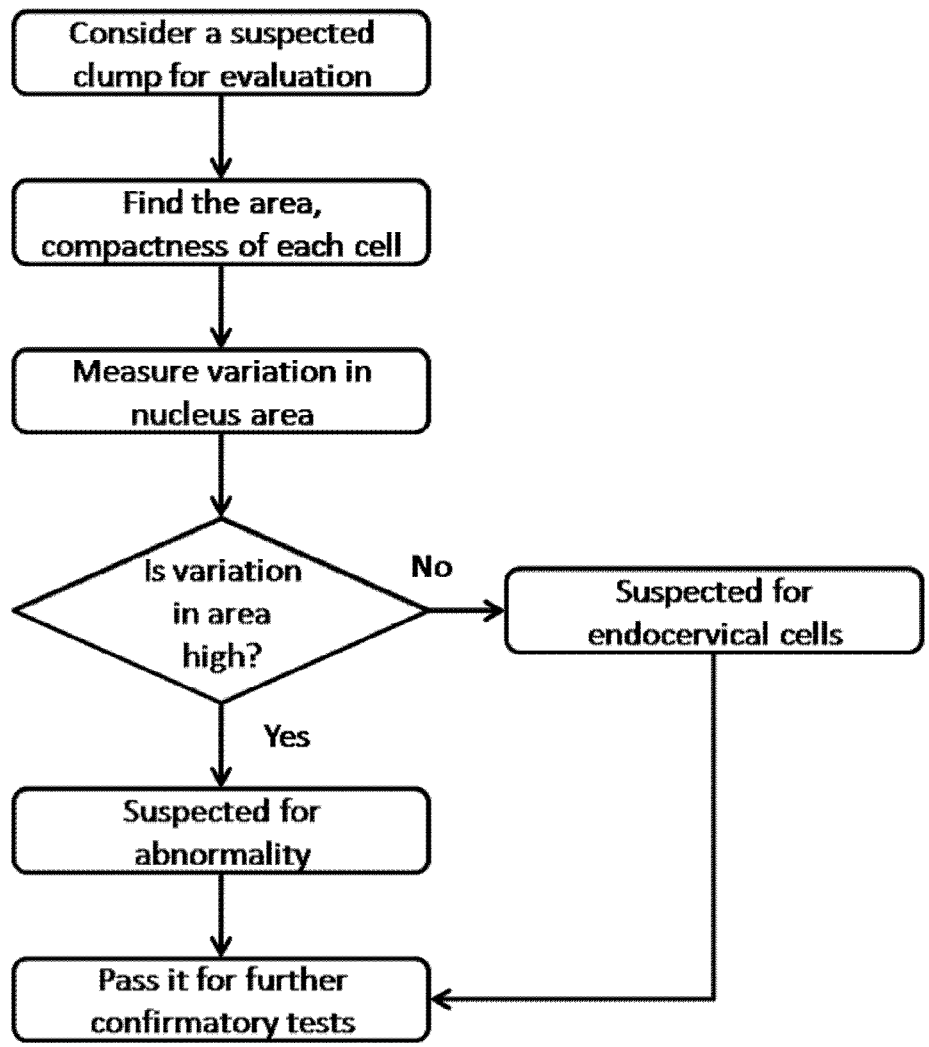
FIG. 2 shows a flow diagram for distinguishing whether or not identified cell aggregates comprise abnormal cells or normal cells (termed "endocervical cells" here, which is, strictly speaking, clinically imprecise, because endocervical cells can also become malignant).

FIGS. 1 and 2 show flow charts which have been described in the text already.

Figure 3:
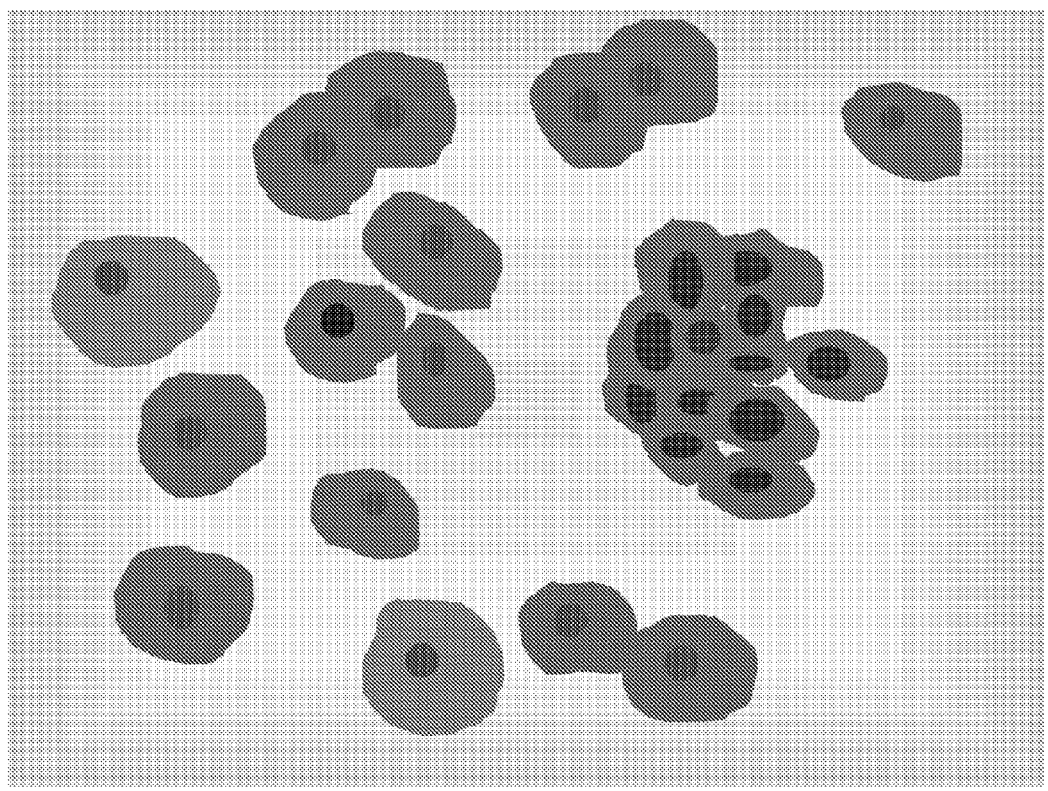
FIG. 3 shows an artificially created example of a Pap smear image created to explain the envisaged concept.

FIG. 3 shows an artificially created example of a Pap smear image to explain the concept of the present invention. In the case of abnormal cells the cytoplasm parts of the cells stick together, and the nuclei of the cells are very close to one another (small inter-nuclei distance).

In contrast thereto, normal cell nuclei are not close to one another even if the cytoplasm parts of these cells contact each other. This is a unique feature that has been observed in many images from different slides imaged as a part of the research project which stands behind the present invention.

Inter-nuclei distance mapping is thus used in the algorithmic identification process to identify abnormal cells, particularly in those regions of interest which have earlier been identified, by cell aggregation analysis, as suspicious.

It has been observed that cells which have only a small risk to become cancerous also tend to form aggregates. In this case, the variability in nucleus size between endocervical cells and abnormal cells from the ectocervix can be used as a distinguishing feature, because in abnormal cell aggregates the nucleus size varies widely whereas in normal cell aggregates the nucleus sizes remain uniform.

Figure 4:
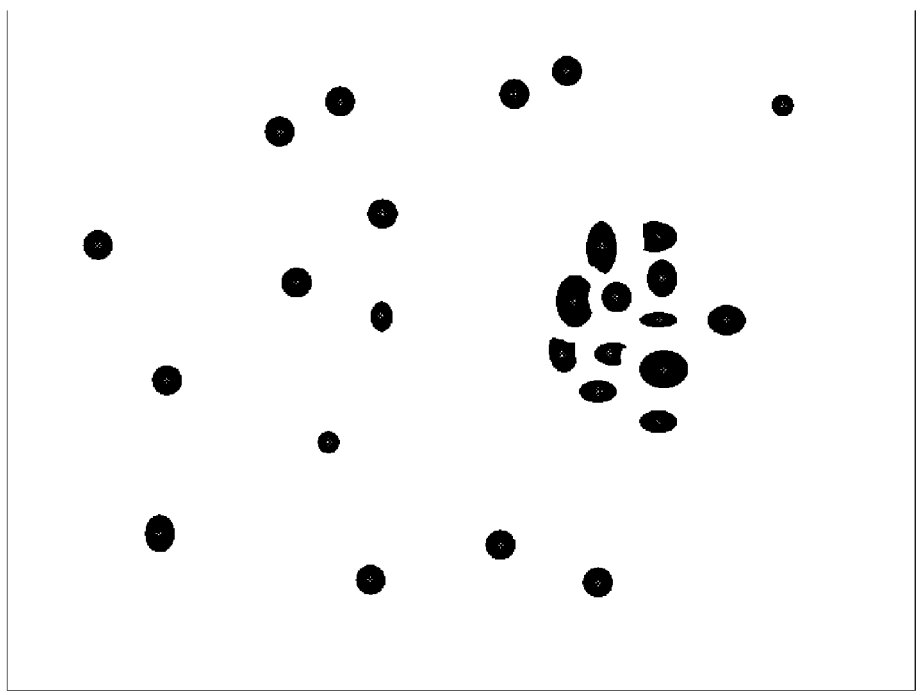
FIG. 4 shows the segmentation of the cells and the corresponding nuclei.

FIG. 4 shows the result of the segmentation of the cells and the corresponding nuclei. Based on the subsequent algorithms, regions of interest can be determined which are highly suspicious to comprise abnormal cells.

Figure 5:
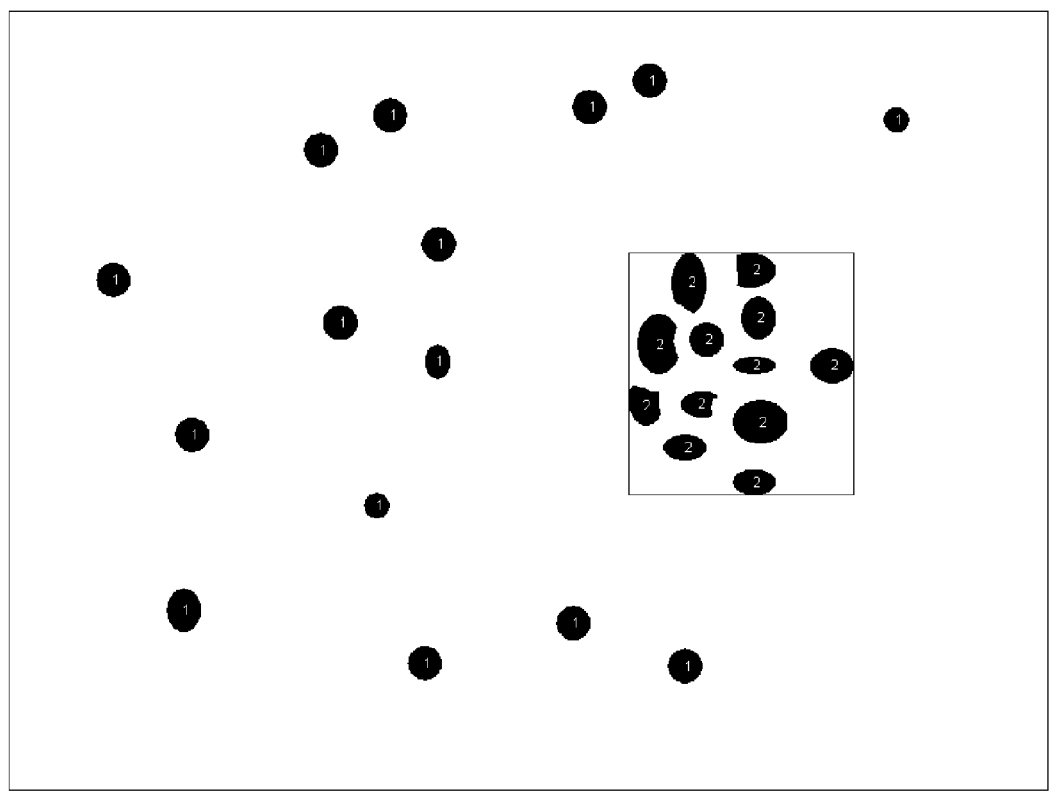
FIG. 5 shows results after clustering, i.e., the cluster number and an inner rectangle showing the region of interest for possible abnormality.

FIG. 5 shows the results of such process clustering. Two different clusters have been identified, wherein cluster No 2—marked by a rectangle—is likely to comprise abnormal cells, due to (i) extensive cell clustering, (ii) high variation of nuclei sizes, and (iii) small inter-nuclei distances.

Figure 6:
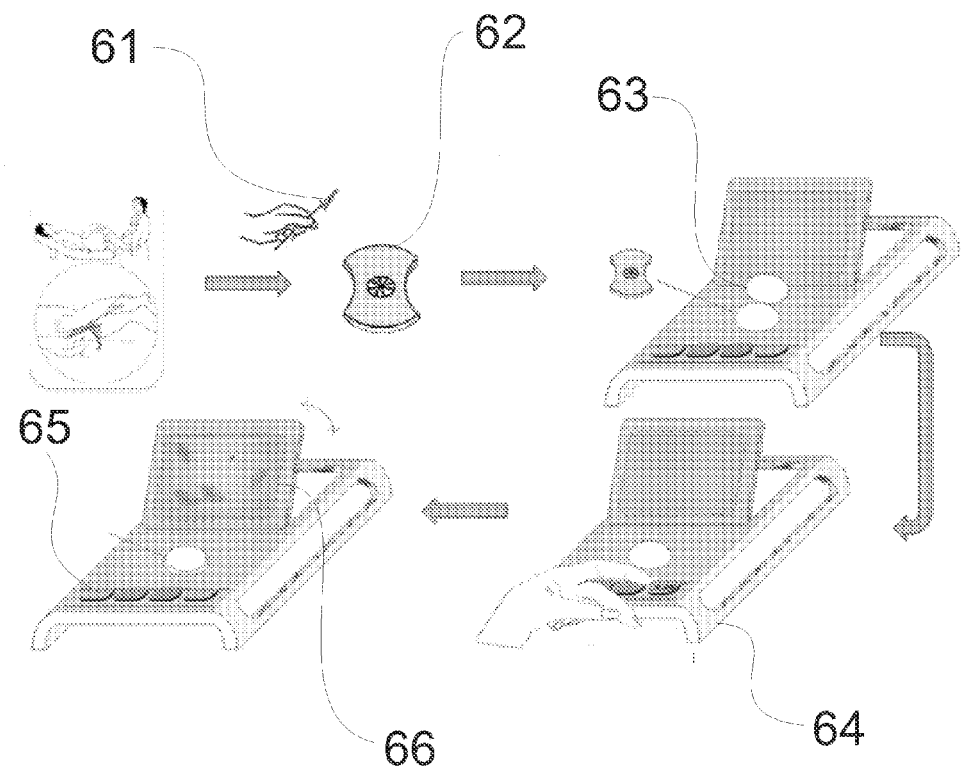
FIG. 6 shows the envisaged system according to the invention, and its work flow.

FIG. 6 shows a system and work flow according to the present invention. The sample is collected by means of a sample collector 61, which may adopt the shape of a brush, similar to a Q-tip, and is transferred to a cartridge 62 which is disposed for placement in the sample receiving unit 63 of a device 64 according to the invention. The device is shown in form of a portable point of care device. Optionally, the sample can be stained in between. The sample is then scanned by the optical magnification unit and the image acquisition device unit present in the device. Upon actuation of an input means 65, which is embodied, herein, as an array of keys, the device acquires an image from the sample in the cartridge and passes it to the algorithm embedded into the system. Then, the method steps according to the invention are accomplished, and results of the analysis are shown on output means 66, which is embodied, herein, as a display screen.

Figure 7:
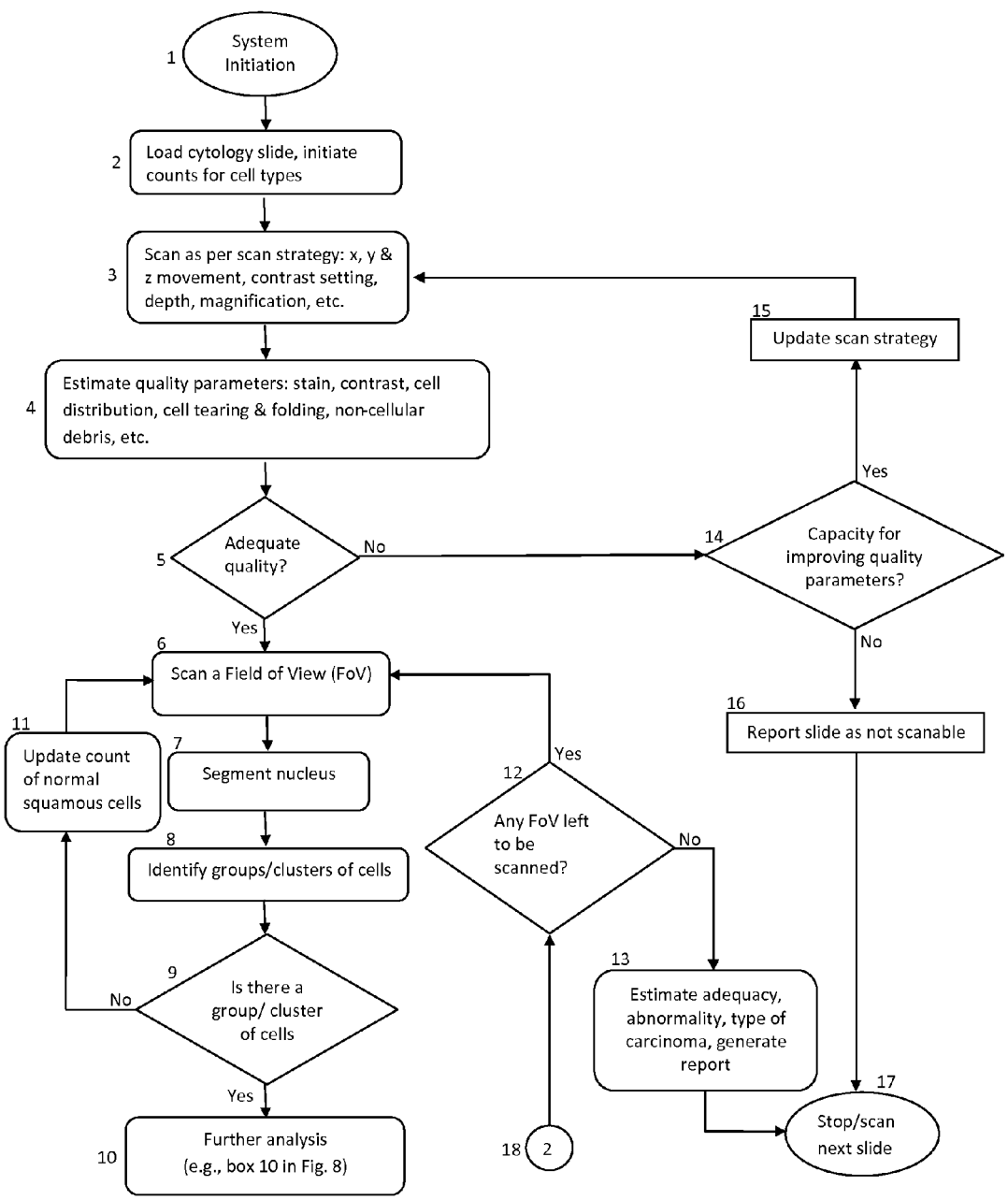
FIGS. 7 and 8 show flow diagrams comprising an alternative approach to identify regions of interest.
Figure 8:
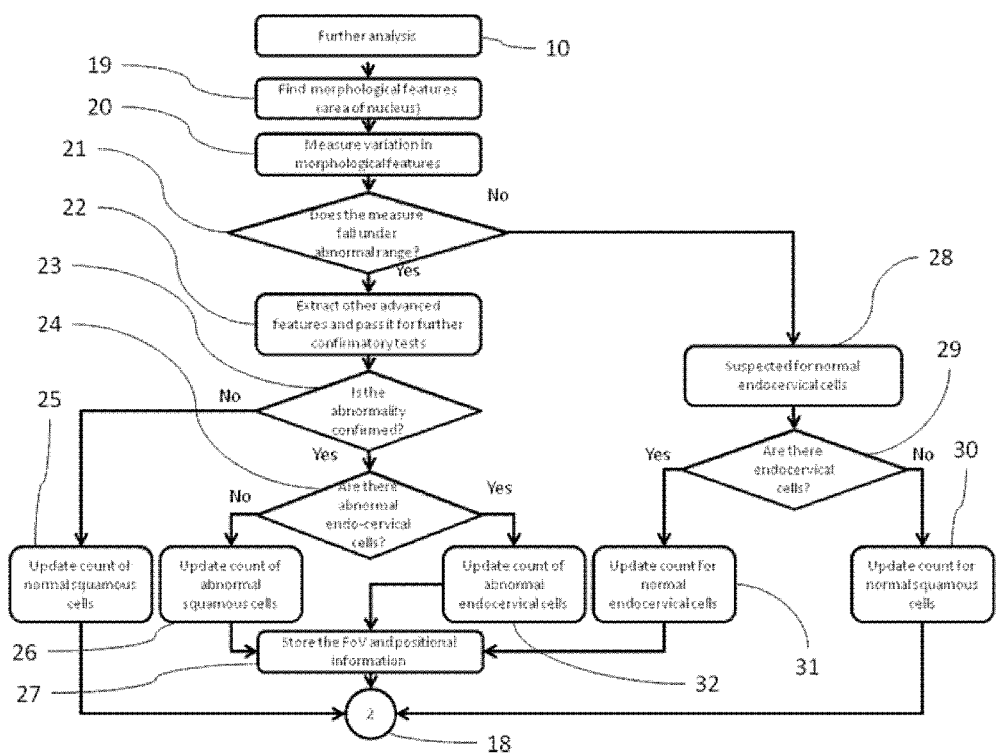
Figure 9:
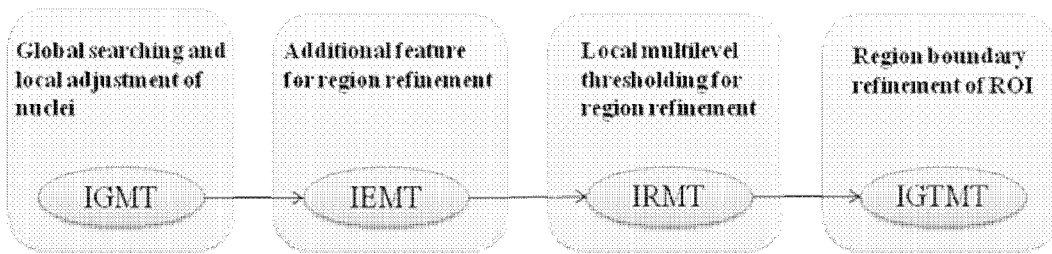
FIG. 9 shows the Evolution of the Pap-smear nucleus segmentation techniques, from IGMT and IEMT to IGTMT and IRMT.
Figure 10:
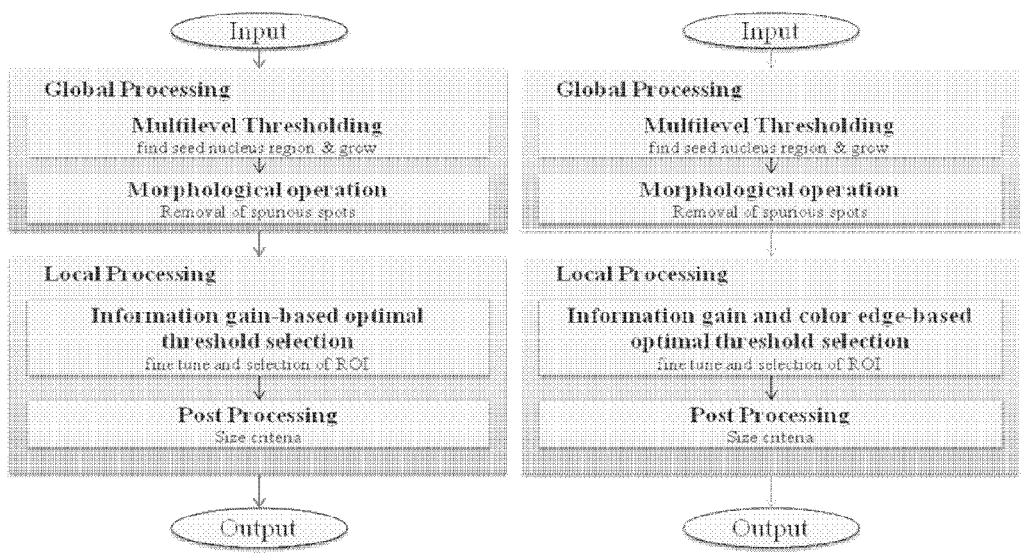
FIG. 10 shows flow diagrams of (A) IGMT and (B) IEMT technique for Pap-smear nucleus segmentation.
Figure 11:
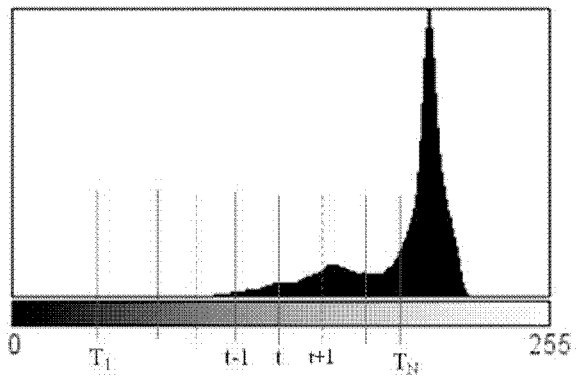
FIG. 11 shows multiple threshold levels in in a Papsmear image histogram, and the resulting segmentation.
Figure 11:
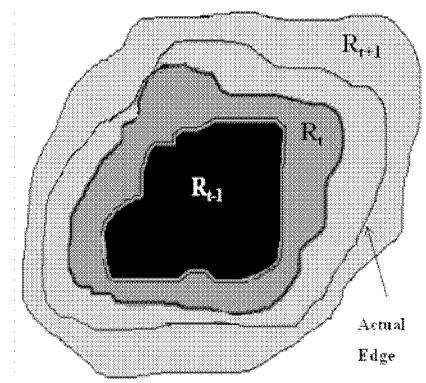
Figure 12:
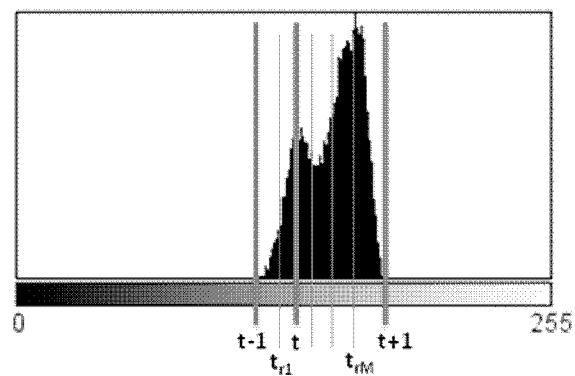
FIG. 12 shows again multiple threshold levels in in a Papsmear image histogram, and the resulting segmentation.
Figure 12:
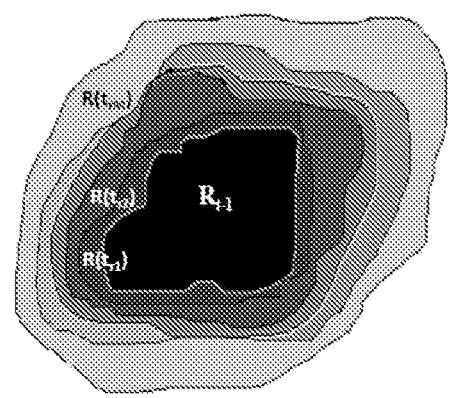
Figure 13:
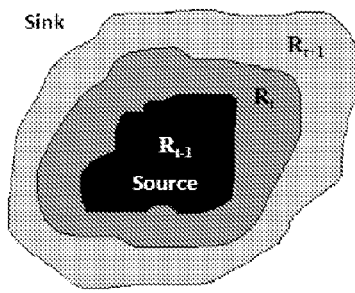
FIG. 13 shows $R_{t-1}$ and outside the region $R_{t+1}$ presented as source and sink respectively indicating the flow of a directed graph.
Figure 14:
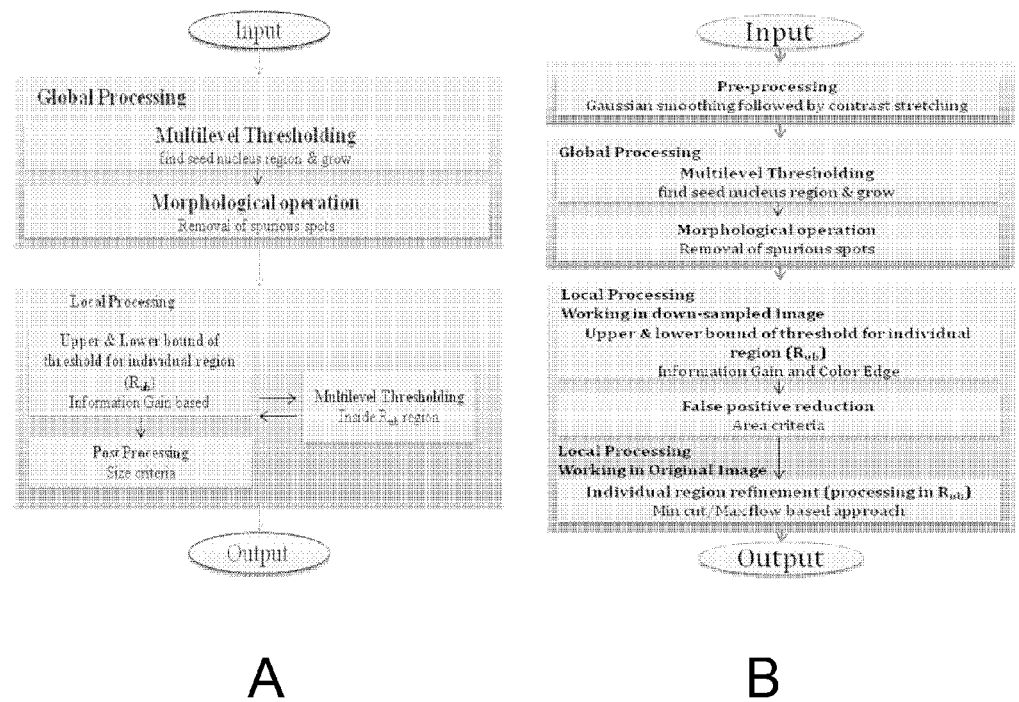
FIG. 14 shows flow diagrams of (A) IRMT and (A) IGTMT for Pap-smear nucleus segmentation.
Figure 15:
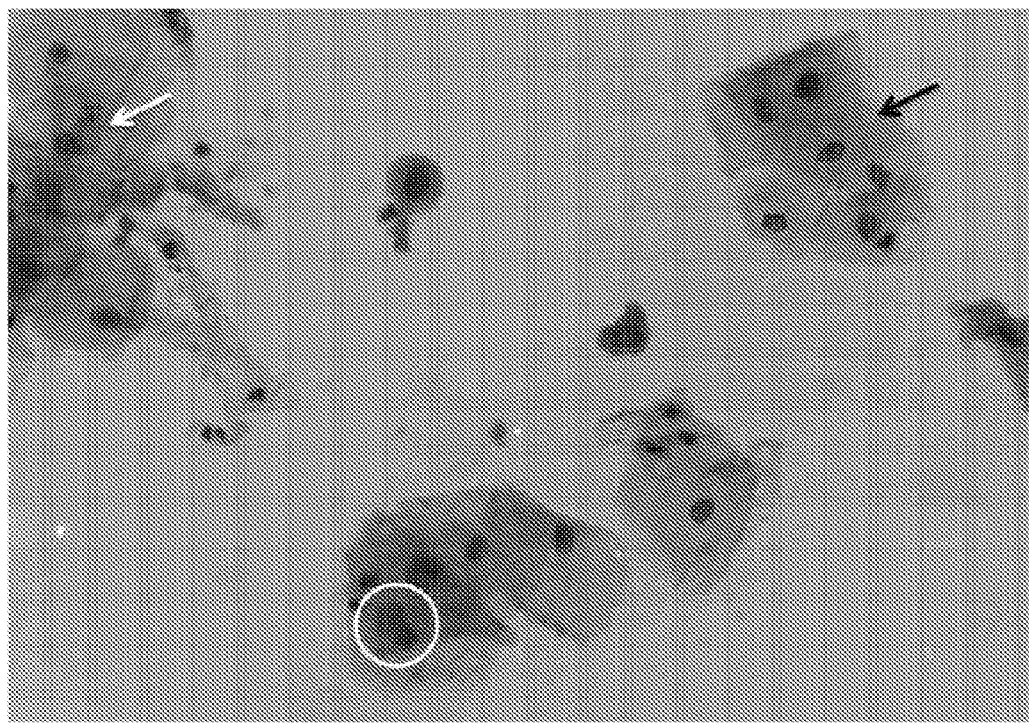
FIG. 15 shows a Pap-smear image showing overlapping nucleus along with their intensity variation (in white circle) and focused region (marked in black arrow) and unfocused region (marked in white arrow).

FIGS. 7 and 8 show flow diagrams comprising a more elaborated approach to identify regions of interest which may be likely to comprise abnormal cells. In FIG. 7 the main focus is to identify the cellular regions and find cell aggregates. Once the latter are identified the algorithm passes the respective field of view to further analysis, as explained in FIG. 8. In Box 1 of FIG. 7, the system initiation is done. Here, essentially, the system resets and arrives at a reference position, clears all the buffers, etc. In Box 2 a cytology sample is loaded, in most cases as a slide (see above), and the initiation for cell count of all type of cells, such as normal/abnormal squamous cells and their types, and normal/abnormal endocervical cells, is initiated, and the respective result is stored. In Box 3, a scan strategy is chosen. The scan strategy involves the selection of step size of the movement of the sample in x and y direction and the focus depth (z direction) relative to the imaging devices (i.e., either the sample or the imaging device is moved), and the selection of magnification, contrast, etc. Further, the system starts reading the sample/slide, and the images are acquired. In Box 4, the quality parameter of the slide/images are estimated. In Box 5, the quality parameters are checked for their adequacy (by comparing with a priori data). If the quality is not adequate, the system goes in the loop to check the scope for up-gradation in Box 13. If there is scope to upgrade the scan strategy (i.e, if the scan parameters are within the defined range of the system), then the system provides an on-the-fly feedback to change the scan strategy (Box 12). If there is no scope for upgrading the scan parameters, a report is generated (Box 14) and the systems stops or goes for the next slide (Box 15).

If in Box 5 the quality is found adequate, then the field of view in Box 6 is passed on for segmentation (Box 7), identification of clusters (Box 9) and verification of clusters (Box 10).

If no clusters are found then it is considered that the actual field of view comprises only normal squamous cell, and their number is counted. Here it should be noted that the cells which are not comprised in clusters are assumed to be normal, given the fact that significant abnormalities are rather found in clustered cells than in isolated cells. If in Box 10 clusters are found, they are suspected for abnormality and the system passes the image of the actual field of view, or other data related to the said clusters, for detailed analysis to link 1 in FIG. 8. If in the respective field of view isolated cells as well as clusters of cells have been determined, the image of the actual field of view, or other data related to the said clusters, are passed for further processing in FIG. 8, while isolated cells are just counted.

After detailed analysis in FIG. 8 (see below) the control is returned back to FIG. 7 at link 2. Here, the system checks if there is any other field of view left to be scanned in Box 11. If yes, the system scans the next field of view and repeats the above described process. If all the fields of view are completed the system generates a report on the actual sample (estimation of abnormality, its severity, type of carcinoma, number of cells etc.) and stops, or moves to the next sample in Box 16.

Images of a field of view comprising clusters, or other data related to the said clusters, are then passed on to the algorithm in FIG. 8. Here a more detailed analysis on the clusters is made. The morphological features in each cell of a given cluster are extracted to measure the variability of these features (Box 2 and Box 3). If the measurements are not in an abnormal range (Box 4), then the cell cluster is suspected to comprise normal endocervical cells (Box 11), hence a confirmatory test is done (Box 12). If the assumption is true then the count of normal endocervical cells is done in Box 14. If not, the sample is considered to comprise squamous cells, and a count for squamous cells is done in Box 13. Further, for endocervical cells, their geometric co-ordinates in the sample and the corresponding field of view are stored because of their importance in interpretation according to the Bethesda system, which is a system for reporting cervical or vaginal cytologic diagnoses used for reporting Pap smear results. This will also help in reviewing the sample, or its image, by a pathologist/cytologist at a later time.

If, in Box 4, it is decided that the measurements fall under an abnormal range, additional advanced features (such as intensity variation, texture, fractal dimension of the nuclear boundary, jazziness of the membrane, etc.) are extracted in Box 5 and a confirmatory test is done in Box 6. If in Box 6 the abnormality of the clusters is not confirmed, then the cells are considered to be normal squamous cells, hence, their count is updated in Box 8 and the control returns back to link 2 in FIG. 7. If, in Box 6, the abnormality of the cluster under consideration is confirmed it is further tested whether these cells are abnormal squamous cells or abnormal endocervical cells (Box 7). If they are not endocervical cells, the count of abnormal squamous cells is updated in Box 9. Otherwise, the count of abnormal endocervical cells is updated (Box 15). The geometric co-ordinates in the slide and the corresponding field of view is stored for these categories of cells and the control returns back to link 2 in FIG. 7.

The invention claimed is:

1. A method for the detection of abnormalities in a patient's biological sample comprising cells, which method comprises at least the following steps:
   a) acquiring a digital image of said sample by digital image acquisition;
   b) selecting a field of view in the digital image;
   c) optically detecting, by digital image processing, whether or not, in said field of view, cell aggregates exist;
   d) if, in step c), the detection of cell aggregates is negative selecting a new field of view and repeating steps b) and c) until cell aggregates are detected;
   e) if, in step c), the detection of cell aggregates in the field of view is affirmative, classifying the sample as one of "likely to comprise abnormal cells" or "likely to comprise normal cells", including:

e1) classifying the sample as "likely to comprise abnormal cells" if the degree of variation of a major axis or a minor axis or a ratio of the major and minor axes of ellipses encircling at least one morphological feature including at least two cells statistically is greater than a first threshold established by multilevel thresholding, or e2) classifying the sample as "likely to comprise normal cells" if the degree of variation of the major axis or the minor axis or the ratio of the axes of the ellipses encircling said feature of the at least one morphological feature statistically falls below the first threshold wherein said morphological feature is at least one selected from the group consisting of:
cell nucleus size or area,
regularity of shape of a cell and a cell nucleus,
size ratio of cytoplasm to nucleus, and
ratio of areas of cytoplasm and nucleus; and wherein the biological sample is a cervical sample comprising endocervical cells and ectocervical cells.

2. The method according to claim 1, wherein said threshold established by multilevel thresholding is established by at least one technique selected from the group consisting of:
Information Gain-based Multilevel Thresholding technique,
Information gain and color Edge-based Multilevel Thresholding technique,
Information gain-based Recursive Multilevel Thresholding technique, and
Information and Graph Theory-based Multilevel Thresholding technique.

3. The method according to claim 1, wherein the at least one morphological feature is selected from the group consisting of:
brightness intensity variation within a cell and/or a cell nucleus,
jazziness of a cellular membrane,
texture, and/or
fractal dimension of the nucleus.

4. The method according to claim 1, further comprising:
biomarker testing said biological sample from said patient, or a new biological sample from said patient;
human papilloma virus deoxyribonucleotide acid (HPV DNA) testing said biological sample or said new biological sample;
wherein the testing indicates the presence of or predisposition for cervical cancer in the patient.

5. The method according to claim 1, wherein the image acquisition is carried out by means of a diagnostic imaging scanner.

6. The method according to claim 1, wherein the image acquisition is carried out by means of an optical magnification device.

7. The method according to claim 1, wherein steps b)-e2) are carried out while the digital image acquisition is still in process.

8. The method according to claim 1, wherein step c) comprises at least the steps of:
segmenting cell nuclei present in the cell aggregates imaged in the field of view, and
determining the centroids of each cell in the cell aggregates.

9. The method according to claim 1, further comprising at least one step selected from the group consisting of:
classifying cells comprised in the sample which are "likely to comprise normal cells" as "normal endocervical" or "normal ectocervical", and
classifying cells comprised in the sample which are "likely to comprise abnormal cells" as "abnormal endocervical or "abnormal ectocervical";
wherein endocervical describes squamous cells; and
wherein ectocervical describes columnar cells.

10. The method according to claim 1, further comprising the step of
counting each classified cell type.

11. The method according to claim 1, wherein the biological sample comprises cells selected from the group consisting of:
a smear sample,
a tissue slice,
a liquid sample,
a fine needle aspiration cytology sample, and
an abrasive cytology sample.

12. The method according to claim 1, wherein the biological sample comprising cells is stained.

13. The method according to claim 1, wherein steps b)-e2) are carried out while data related to the acquired image, or parts thereof are stored in a volatile memory.

14. A device for the detection of abnormalities in a biological sample comprising cells, the device comprising:
a sample receiving unit configured to receive the biological sample;
a digital image acquisition unit configured to acquire a digital image of the sample in the receiving unit;
a digital image processing unit configured to carry out the method steps according to claim 1,
a user interface comprising at least one output and one input; and
wherein the biological sample is a cervical sample comprising endocervical cells and ectocervical cells.

15. The device according to claim 14 further comprising:
at least one optical magnification unit.

16. The device according to claim 14, further comprising:
at least one electronic interface.

17. The device according to claim 14, further comprising:
at least one sample collector and/or at least one cartridge configured to transfer the sample, said cartridge being configured for placement in the sample receiving unit.

* * * * *